US 8,406,503 B2

(12) United States Patent
Ueda

(10) Patent No.: US 8,406,503 B2
(45) Date of Patent: Mar. 26, 2013

(54) MOUNTED COMPONENT INSPECTION APPARATUS, COMPONENT MOUNTING MACHINE COMPRISING THE MOUNTED COMPONENT INSPECTION APPARATUS, AND MOUNTED COMPONENT INSPECTION METHOD

(75) Inventor: Yoichiro Ueda, Osaka (JP)

(73) Assignee: Panasonic Corporation, Osaka (JP)

( * ) Notice: Subject to any disclaimer, the term of this patent is extended or adjusted under 35 U.S.C. 154(b) by 494 days.

(21) Appl. No.: 12/696,838

(22) Filed: Jan. 29, 2010

(65) Prior Publication Data

US 2010/0189340 A1 Jul. 29, 2010

(30) Foreign Application Priority Data

Jan. 29, 2009 (JP) ................................. 2009-017965
Jan. 25, 2010 (JP) ................................. 2010-012669

(51) Int. Cl.
*G06K 9/00* (2006.01)
(52) U.S. Cl. ....................................... 382/147; 382/141
(58) Field of Classification Search .................. 382/100, 382/141, 145–152; 356/237.1–237.6
See application file for complete search history.

(56) References Cited

U.S. PATENT DOCUMENTS 5,495,424 A * 2/1996 Tokura ............................. 702/82

FOREIGN PATENT DOCUMENTS

JP 2003-110298 4/2003

* cited by examiner

*Primary Examiner* — Tri T Ton
(74) *Attorney, Agent, or Firm* — Hamre, Schumann, Mueller & Larson, P.C.

(57) ABSTRACT

A mounted component inspection apparatus according to the present invention includes: a component library holding inspection information; an inspection processing unit for inspecting a component under inspection using the component library; a match rate acquisition unit for acquiring a match rate indicating the degree to which the inspection information is suitable for the inspection by the inspection processing unit, on the basis of the result of the inspection by the inspection processing unit; and a judgment unit for selecting the inspection information having a higher match rate, of the inspection information before updating and the inspection information after updating. The component library can hold the inspection information before and after updating, and the inspection processing unit carries out the inspection using the inspection information before and after updating held in the component library.

18 Claims, 16 Drawing Sheets

FIG. 6

| No | CONTENTS | AFTER UPDATING | BEFORE UPDATING |
|---|---|---|---|
| 1 | SIZE VARIATION SEARCH VALUE Xmin | −80.0 | −100.0 |
| 2 | SIZE VARIATION SEARCH VALUE Xmax | 80.0 | 100.0 |
| 3 | SIZE VARIATION SEARCH VALUE Xstep | 40.0 | 20.0 |
| 4 | SIZE VARIATION SEARCH VALUE Ymin | 0.0 | 0.0 |
| 5 | SIZE VARIATION SEARCH VALUE Ymax | 0.0 | 0.0 |
| 6 | SIZE VARIATION SEARCH VALUE Ystep | 0.0 | 0.0 |
| 7 | ROUGH RECOGNITION LIMIT EVALUATION VALUE | 0.0 | 0.0 |
| 8 | FINE RECOGNITION LIMIT EVALUATION VALUE | 50.0 | 50.0 |
| ... | | | |

FIG. 10

| JUDGMENT OF INSPECTION MACHINE | TRUE RESULT | PROBLEMATIC RESULT |
|---|---|---|
| OK | TRUE NORMALITY | OVERSIGHTS → 0 |
| NG | TRUE DEFECT | EXCESSIVE JUDGMENT |

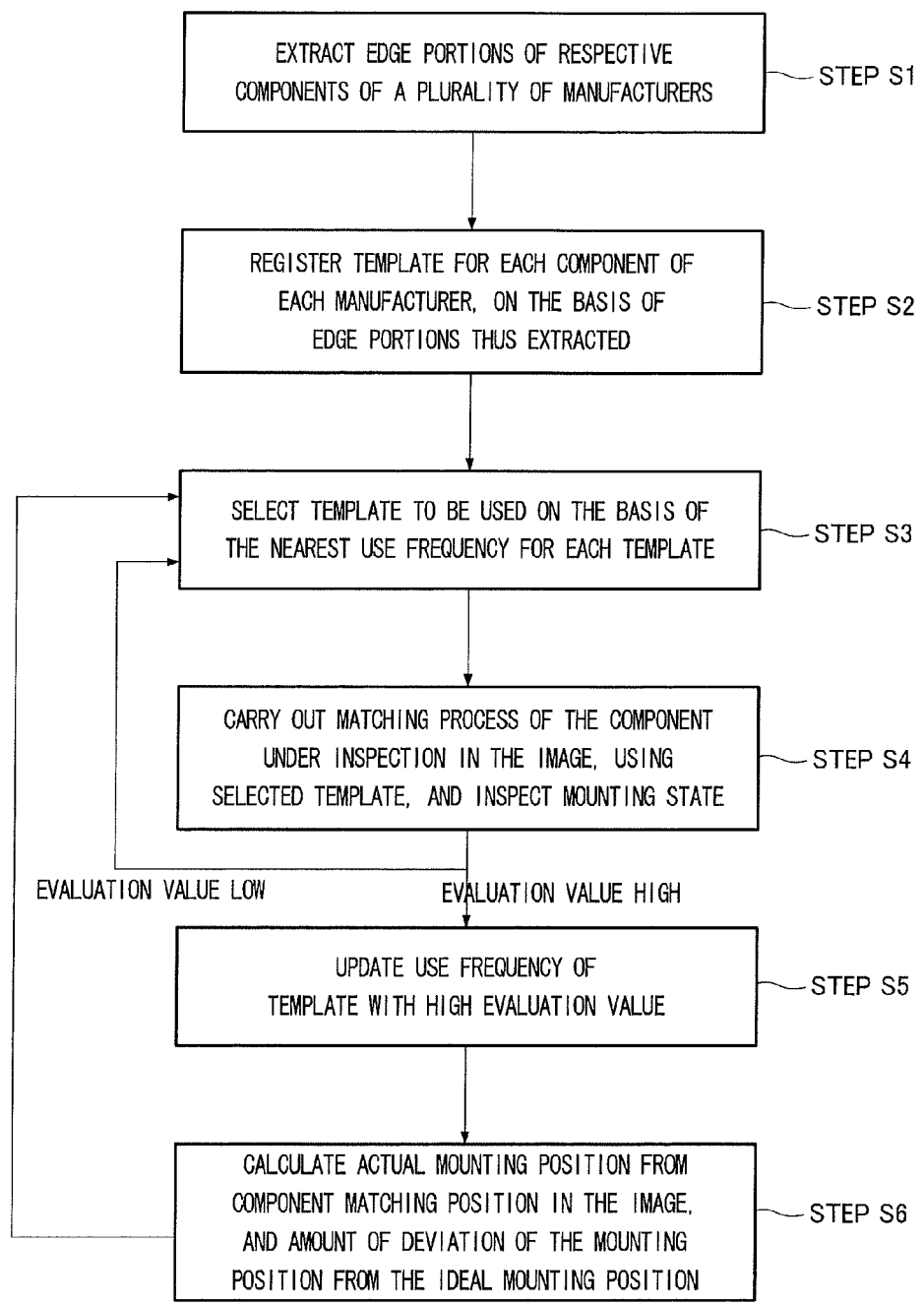

MOUNTED COMPONENT INSPECTION APPARATUS, COMPONENT MOUNTING MACHINE COMPRISING THE MOUNTED COMPONENT INSPECTION APPARATUS, AND MOUNTED COMPONENT INSPECTION METHOD

The disclosures of Japanese Patent Application No. 2009-017965 filed Jan. 29, 2009 and Japanese Patent Application No. 2010-012669 filed Jan. 25, 2010 including specification, drawings and claims are incorporated herein by reference in its entirety.

BACKGROUND OF THE INVENTION

1. Field of the Invention

The present invention relates to the inspection of mounted components, for inspecting the presence or absence of a component at a prescribed position on a circuit substrate, a deviation from the ideal position of a component mounted on a circuit substrate, whether or not the direction of polarity of a component mounted on a circuit substrate is correct, and so on.

2. Description of the Related Art

Conventionally, the inspection of mounted components is carried out using a template recorded in a component library. Furthermore, one type of the mounted component inspection using a template is an inspection using a master template and a spare template, which is disclosed in Japanese Patent Application Publication No. 2003-110298. In the inspection disclosed in Japanese Patent Application Publication No. 2003-110298, when, for instance, there is low coincidence between a mounted component and the master template, then the template used is switched from the master template to the spare template. By switching between the master and spare templates in this way, the inspection takt time is improved, in other words, the inspection time is shortened.

FIG. 15 shows the composition of a mounted component inspection apparatus disclosed in Japanese Patent Application Publication No. 2003-110298. FIG. 16 is the flowchart of a mounted component inspection method disclosed in Japanese Patent Application Publication No. 2003-110298. Below, the conventional inspection of mounted components as disclosed in Japanese Patent Application Publication No. 2003-110298 will be described with reference to FIG. 15 and FIG. 16.

Firstly, the conventional mounted component inspection apparatus will be described with reference to FIG. 15.

In FIG. 15, a camera 1 captures an image of a substrate 3 mounted on a stage 2. The substrate 3 is a circuit substrate, for example. A component 4 is mounted on the substrate 3. The component 4 is an electronic component, for example. Furthermore, illumination light is irradiated onto the substrate 3 from an illumination unit 5. The image captured by the camera 1 is input to an image processing unit 7 via an imaging unit 6. The imaging unit 6 corrects the brightness of the image captured by the camera 1 and converts the scale of the image from meter units to pixel units.

By processing the image input via the imaging unit 6, the image processing unit 7 performs the inspection of the state of mounting, such as the inspection of whether or not there is a component at a prescribed position on the substrate 3, inspection to confirm whether or not an incorrect component other than a prescribed component has been mounted at a prescribed position on the substrate 3, inspection of the position of the mounted component 4, and inspection of the amount of deviation of the mounted component 4 from an ideal mounting position.

More specifically, the image processing unit 7 comprises: an edge portion extraction unit 8, a template composition/registration unit 9, a matching calculation unit 10, a component position measurement unit 11, a template selection unit 12 and a template use frequency updating/storage processing unit 13.

The edge portion extraction unit 8 extracts the edge portions of electrode portions, which are one portion of the outline of the component under inspection, from the input image. The template composition/registration unit 9 composes a template on the basis of the extracted edge portion, and registers the template thus composed in a component library (not illustrated). The matching calculation unit 10 carries out the inspection of the mounting state described above by implementing a matching process on the input image using the registered template. The position of the mounted component 4 and the amount of positional deviation of the component 4 are determined in pixel units. The component position calculation unit 11 converts the position of the component 4 and the amount of positional deviation of the component 4 which have been determined in pixel units, into dimensions in meter units. The template selection unit 12 switches the template used for the matching process. The template use frequency updating/storage processing unit 13 updates the frequency of use of the template, and stores the frequency of use after updating in the component library (not illustrated).

Next, the conventional mounted component inspection method will be described with reference to FIG. 16.

Firstly, at step S1, images of components of manufacturers which are the objects of inspection are captured by the camera 1, and the edge portions of the electrode portions of the components are extracted by the edge portion extraction unit 8. More specifically, the edge portions of the electrode portions apart from the boundary lines between the main portion and the electrode portions of the component are extracted.

Next, at step S2, the template composition/registration unit 9 composes and registers templates for the respective components on the basis of the edge portions thus extracted.

Thereupon, at step S3, the template selection unit 12 selects, from component-specific templates of components which are expected to be mounted, the template with the highest recent use frequency, in other words, the template of the component having the highest probability of being mounted.

Thereupon, at step S4, the matching calculation unit 10 performs the above-described inspection of the mounting state by using the selected template. At this point, if the evaluation value of the matching process such as the degree of coincidence in matching, is lower than a reference value, then the procedure returns to step S3, and the template selection unit 12 automatically switches the template to be used to the template having the next highest frequency of use, and carries out the inspection of the mounting state at step S4, once again. In this way, the template selection unit 12 switches the template to be used to a template having an evaluation value higher than the reference value.

Next, at step S5, the template use frequency updating/storage processing unit 13 updates the frequency of use of the template which has ultimately been used in the matching process.

Thereupon, at step S6, the component position calculation unit 11 calculates, in meter units, the position of the component 4 and the amount of positional deviation of the component 4, which have been determined in pixel units.

From step S6 onwards, the steps S3 to S6 described above are repeated until the completion of the inspection of the whole inspection area where the inspection of the substrate 3 is required.

In this way, in the conventional inspection of mounted components, a template having a high frequency of use is used preferentially. Therefore, the number of switches of the template is reduced statistically, and the time required for the matching process can be shortened. Consequently, the inspection takt time is improved, in other words, the inspection time is shortened.

As described above, in the conventional mounted component inspection, the template used is switched to the template having an actual evaluation value higher than the reference value. However, in this conventional mounted component inspection, if the recognition rate does not improve even when the templates are switched, then even supposing that the component library is adjusted to include template changes, it is not possible to ensure that the component library after this adjustment represents an improvement compared to the component library before adjustment. Here, the recognition rate means the rate of the number of times that correct recognition is made with respect to the number of times that the inspection is performed. Furthermore, false recognition means that correct recognition cannot be performed.

In particular, in a production line in which 1000 or more components are mounted on a single substrate, many components of different types need to be inspected and therefore, a recognition rate of the level of several PPM (parts per million), more specifically, an allowable rate of several false recognitions per million times is required. In a production line of this kind, when the component library is adjusted, any new problems caused by such adjustment do not become apparent simply by confirming whether or not recognition is performed correctly in several substrates immediately after the adjustment of the component library, but rather the satisfactory or unsatisfactory nature of the recognition rate is revealed later on, after the adjusted component library has been introduced. When the poor recognition rate becomes apparent, the adjusted component library has to be adjusted again at that point and returned to the original component library.

In this way, in the conventional mounted component inspection, since there is no means of confirming quantitatively that an improvement in the performance of the component library has been achieved by adjustment, then it has taken time until the level of this performance can be assessed, and therefore it has required time to re-adjust the component library. Moreover, since it takes time until the satisfactory or unsatisfactory nature of the recognition rate is revealed, then unless similarities and differences between the component library before adjustment and the component library after adjustment are managed suitably, the time taken to re-adjust the library in order to return to the original component library progressively increases.

These problems are especially pronounced in cases where many different types of components are mounted, and where there is a plurality of component libraries requiring adjustment. Furthermore, in this case, in the conventional mounted component inspection, since there is no means of confirming the improvement made in the performance of the component library through adjustment quantitatively, then it has been difficult to specify which component library should be adjusted. Furthermore, if there are many different types of components to be mounted, then the management of recording of differences between the component libraries before adjustment and the component libraries after adjustment is complicated, and this places an increased load on the operator.

As described above, in the conventional mounted component inspection, it has not been possible to re-adjust the component libraries quickly.

Furthermore, in the mounted component inspection, the shape of the object under inspection is not uniform, but rather includes a plurality of shapes. Therefore, creating and improving the component libraries, which is a key requirement for the inspection, need a high level of expertise. However, recently, specialist operators having sufficient expertise are not necessarily present in component mounting sites, and therefore it is necessary to improve the performance of the component libraries in consideration of this situation in the field.

SUMMARY OF THE INVENTION

The present invention has been devised in view of the conventional problems described above, an object thereof being to provide a mounted component inspection apparatus which can rapidly incorporate suitable component libraries in the inspection of mounted components, a component mounting machine which includes this mounted component inspection apparatus, and a mounted component inspection method.

In order to achieve the aforementioned object, the mounted component inspection apparatus according to the present invention comprises: an inspection processing unit for inspecting a component under inspection by using a component library holding updatable inspection information to be used in the inspection of the component under inspection; a match rate acquisition unit for acquiring a match rate that indicates the degree to which the inspection information is suitable for the inspection by the inspection processing unit, on the basis of the result of the inspection by the inspection processing unit; and a judgment unit for selecting the inspection information having a higher match rate, of the inspection information before updating and the inspection information after updating. Furthermore, the component library is capable of holding the inspection information before and after updating, and the inspection processing unit carries out the inspection using the inspection information before and after updating held in the component library, and when the selection is made by the judgment unit, the inspection processing unit carries out the inspection using the inspection information selected by the judgment unit.

According to a desirable embodiment of the present invention, it is possible to confirm, quantitatively, whether the performance of a component library has been improved by adjustment, and it is possible to introduce a suitable component library rapidly. The present invention can also be applied to device inspections in the field of semiconductors, for example, as well as the inspection of mounted components in a production line for mounting components on a substrate.

BRIEF DESCRIPTION OF THE DRAWINGS

FIG. 6 is a diagram showing a display which indicates points of difference in recognition parameters before and after adjustment in the first embodiment of the present invention;

FIG. 10 shows the table of results of an inspection by a mounted component inspection machine according to the second embodiment of the present invention;

FIG. 16 is the flowchart of a conventional mounted component inspection method.

DESCRIPTION OF THE PREFERRED EMBODIMENTS (First Embodiment)

Figure 1:
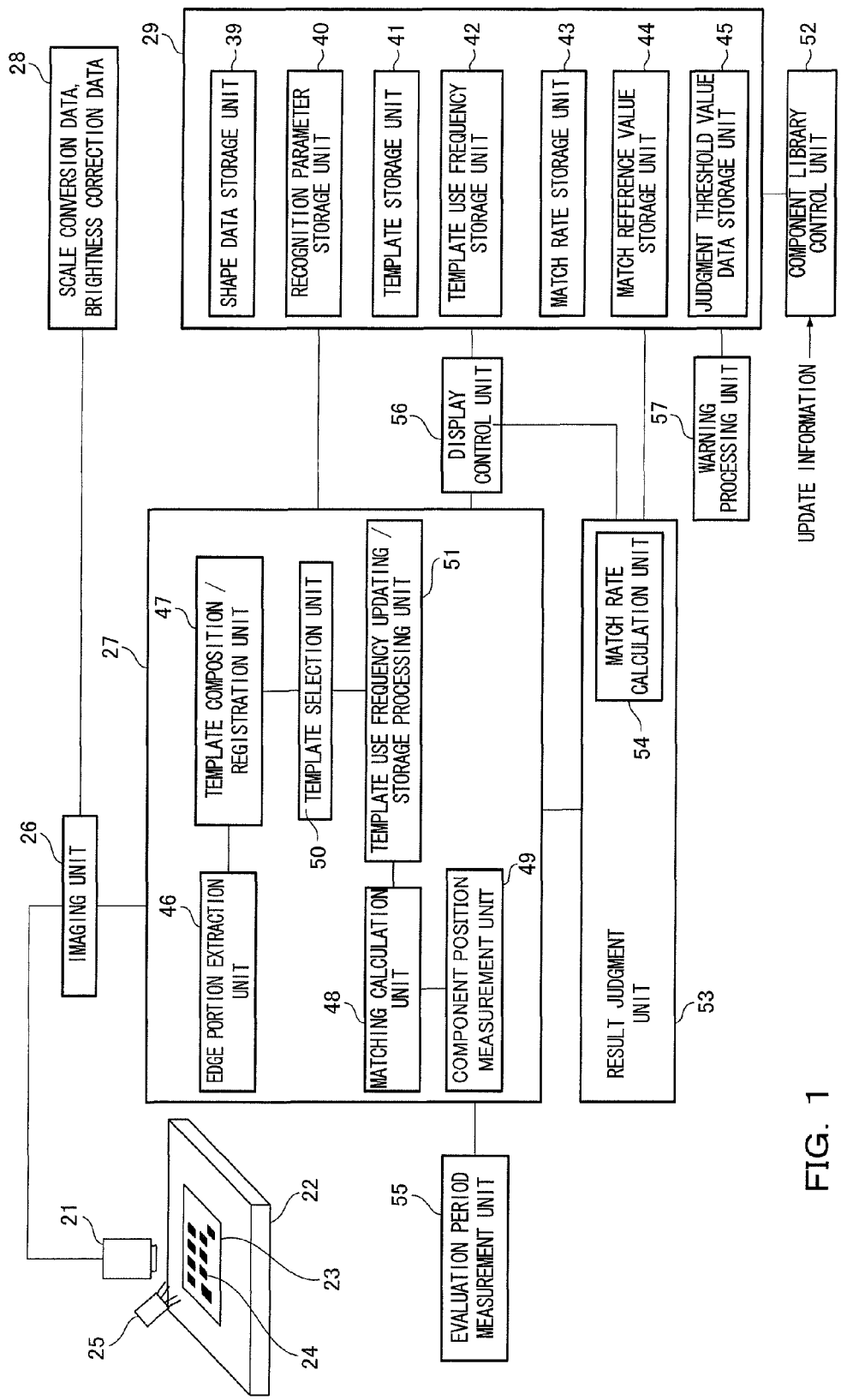
FIG. 1 is a diagram showing the overview of the composition of a mounted component inspection apparatus according to a first embodiment of the present invention.

A first embodiment of the present invention is described in detail with reference to the drawings. FIG. 1 is a diagram showing the overview of the composition of a mounted component inspection apparatus according to the first embodiment of the present invention.

In FIG. 1, a camera 21 captures an image of a substrate 23 mounted on a stage 22. The substrate 23 is a circuit substrate, for example. A component 24 is mounted on the substrate 23. The component 24 is an electronic component, for example. Furthermore, illumination light is irradiated onto the substrate 23 from an illumination unit 25. The image captured by the camera 21 is input to an image processing unit 27 via an imaging unit 26. The imaging unit 26 converts the scale of the image captured by the camera 21 from meter units to pixel units, and corrects the brightness of the image, by using scale conversion data and brightness correction data stored in an equipment specific data storage unit 28. The scale conversion data indicates the resolution of the camera 21 and the brightness correction data indicates the illumination and lens characteristics.

The image processing unit 27 is one example of an inspection processing unit. The image processing unit 27 carries out a mounted component inspection by processing the image input via the imaging unit 26, using an in-equipment component library stored in a component library storage unit 29.

Figure 2:
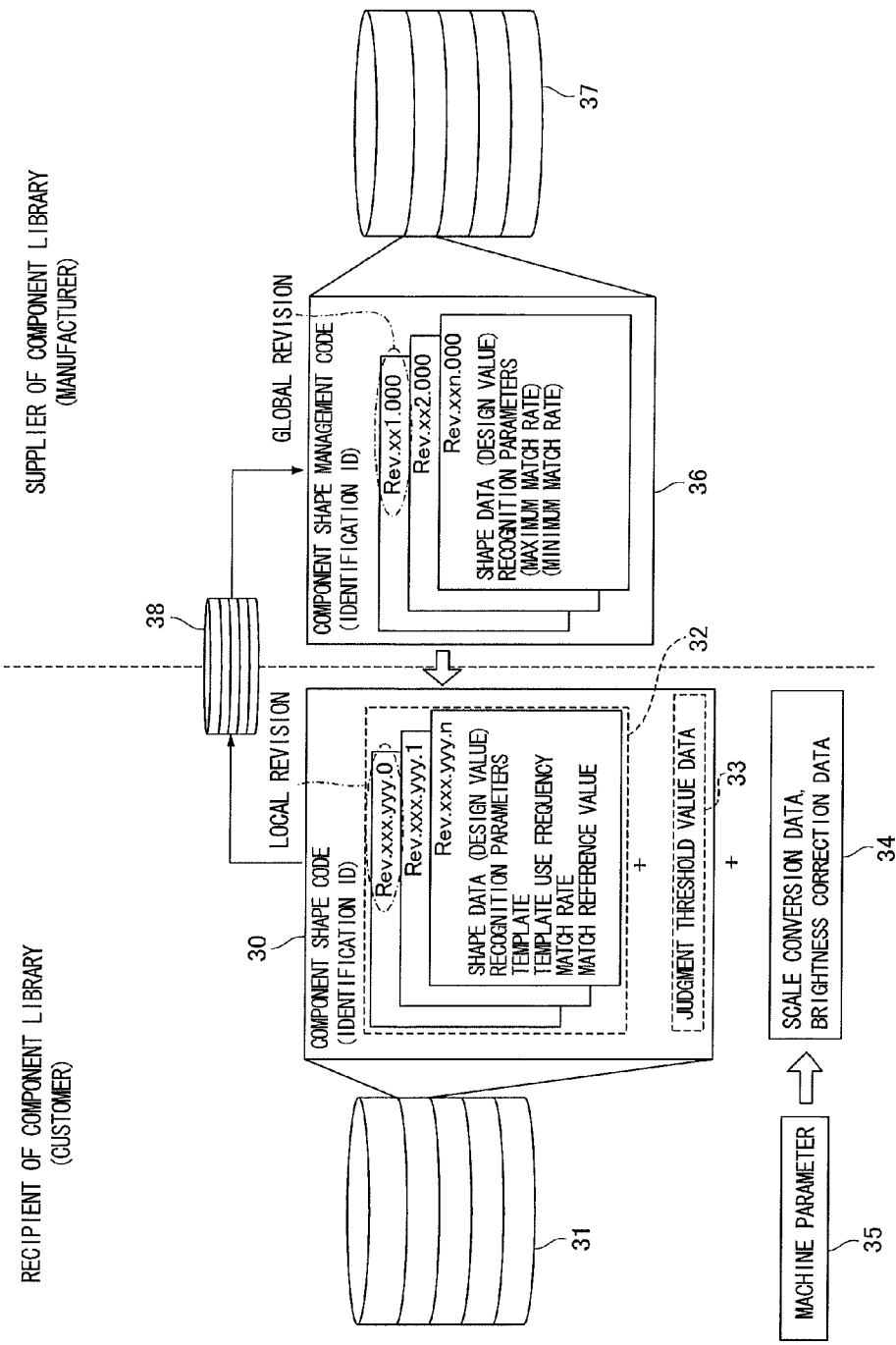
FIG. 2 is a diagram showing the overview of the composition of a component library according to the first embodiment of the present invention.

Here, the in-equipment component library will be described. FIG. 2 is a diagram showing the overview of the composition of a component library according to the first embodiment of the present invention.

In FIG. 2, an in-equipment component library 30 is created for each component from each manufacturer. This is because even components having the same electrical properties have slight differences in component shape between manufacturers.

The in-equipment component library 30 is held in an in-equipment component library database 31. The in-equipment component library database 31 holds the in-equipment component libraries 30 of all components having different shapes. Normally, in a general worksite, the number of component libraries held in the database exceeds 100. The in-equipment component library 30 can be searched for and located in the in-equipment component library database 31 by using a component shape code as an identification ID.

The in-equipment component library 30 is made up of in-equipment component specific data 32 and judgment threshold value data 33. The in-equipment component specific data 32 is one example of information for inspection, and can be updated. The judgment threshold value data 33 indicates a judgment reference for the inspection result produced by the image processing unit 27, which is described hereinafter. Of course, it is also possible to update the judgment threshold value data 33.

The in-equipment component specific data 32 is made up of shape data, recognition parameters, a template, a template use frequency, a match ratio and a match reference value. Here, the template and the template use frequency used can be the same as those disclosed in Japanese Patent Application Publication No. 2003-110298, which is described above. Furthermore, the shape data is based on the design dimension data of the component in question. The recognition parameters serve to recognize the component in question. The recognition parameters include parameters based on the variation tolerances of size of the component in question. By means of these recognition parameters, it is possible to change the shape data and template in accordance with the variation tolerances. Furthermore, the match ratio indicates the extent to which the in-equipment component specific data 32 is suitable for the inspection of the component in question. The match reference value serves to judge whether or not the match ratio is satisfactory.

Furthermore, the in-equipment component library 30 can hold, simultaneously, in-equipment component specific data 32 after updating and in-equipment component specific data 32 before updating, and the image processing unit 27 is capable of inspecting the mounting state of the component in question, by using both of the simultaneously held sets of the in-equipment specific data 32 before and after updating while switching between the in-equipment specific data 32 before and after updating.

Furthermore, the in-equipment component library 30 has a structure for holding only the data required for the inspection of the component, and therefore any conditions which are dependent on the equipment can be eliminated. More specifically, the in-equipment component library 30 is separated from equipment specific data 34, which is specific data for each inspection equipment. By this means, rather than being data which is specific to each inspection equipment, the in-equipment component library 30 is data which can be separated from the inspection equipment and managed uniformly.

The equipment specific data 34 is made up of the scale conversion data and brightness correction data described above. The scale conversion data and brightness correction data are included in equipment specific machine parameters 35 which are information required to operate the equipment. In addition to the scale conversion data and the brightness correction data, the machine parameters 35 also include, for example, a machine offset, drive shaft speed, acceleration and deceleration rate, timer value, and so on.

The scale conversion data which indicates the camera resolution is used because there is a possibility of slight differences in camera resolution between inspection equipment. The differences in camera resolution arise due to the multiplication of slight tolerances in the mechanisms and optics systems of individual inspection equipment. For example, even if the design resolution is 18 μm, it is sufficiently possible that the camera resolution of machine A is 18.100 μm/pixel and the camera resolution of machine B is 18.200 μm/pixel.

In the inspection processing system, as is widely known, calculation for image processing is carried out in pixel units and therefore, it is necessary to convert the scale of the image obtained by imaging the components or substrate, from meter units to pixel units. Consequently, the differences in camera resolution may cause machine errors (differences between inspection equipment).

Therefore, in this mounted component inspection apparatus, the differences in camera resolution between inspection equipment are absorbed by using the scale conversion data. This scale conversion data serves to absorb machine differences and is therefore held in each inspection equipment. The data relating to the dimensions held in the in-equipment component library 30 is limited to data in meter units, and the scale conversion data required for converting the scale to pixel units is clearly separated from the in-equipment component library 30.

The reason that brightness correction data indicating illumination and lens characteristics is used is similar to the reason that the scale conversion data is used. In other words, there is a possibility that differences in brightness between inspection equipment can cause differences in inspection performance between inspection equipment. In particular, there is a high possibility that differences in the fluctuation of illuminance distribution in a two-dimensional plane, which are caused by slight differences in the optics systems in the two-dimensional image processing system, will create differences in inspection performance.

Therefore, in this mounted component inspection apparatus, the differences in brightness between inspection equipment are absorbed by using the brightness correction data. Actually, if inspection equipment which cannot absorb the differences in the illuminance distribution is used, then the adjustment of brightness is implemented in each inspection equipment. Similarly to the scale conversion data, this brightness correction data is held in each inspection equipment in order to absorb machine differences.

The in-equipment component library 30 described above is held by the recipient of the component library such as a customer. On the other hand, an administrator, who performs the overall management of suppliers of the component libraries such as inspection machine manufacturers or of the component libraries (hereinafter, called a component library supplier or supplier), holds reference component libraries 36 for all of the components of different shapes which are under his or her management. All of the adjustments which have been made hitherto are held in the reference component libraries 36. Furthermore, the reference component libraries 36 are held in a reference component library database 37. The reference component library 36 can be searched for and located in the reference component library database 37 by using a component shape management code as an identification ID.

The reference component library 36 holds shape data and recognition parameters, similarly to the in-equipment component library 30, but does not hold a template. This is because a template is created by actually capturing an image of a component by the recipient of the component library. For similar reasons, the reference component library 36 does not include a template use frequency, either.

Furthermore, while the in-equipment component library 30 includes real-time information such as the match rate, the reference component library 36 includes the maximum value and minimum value parameters which have previously been obtained for the match rate held in the in-equipment component library 30 corresponding to the reference component library 36. These parameters are updated whenever a notification is received from the recipient, if the match rate contained in the in-equipment component library 30 of the recipient, which changes in real time, has exceeded the maximum value which has previously been obtained, or has fallen below the minimum value which has previously been obtained.

Furthermore, the in-equipment component library 30 includes the judgment threshold value data 33, but the reference component library 36 does not contain judgment threshold value data. The judgment threshold value data is specified on the basis of the conditions of the production process and the quality management standards, and is not managed uniformly by the supplier of the component library by nature.

If the component shape code assigned as an identification ID in the in-equipment component library 30 and the component shape management code assigned as an identification ID in the reference component library 36 are different, then the component shape code and the component shape management code are linked in a one-to-one relationship, using a component shape conversion database 38, as shown in FIG. 2. If the component shape code and the component shape management code are the same, then the component shape conversion database is not required.

Next, revision numbers will be described. A revision number is assigned to the in-equipment component specific data 32 held in the in-equipment component library 30. Furthermore, the revision numbers are held in the reference component library 36 and are assigned respectively to the reference component libraries which have previously been adjusted.

Figure 3:
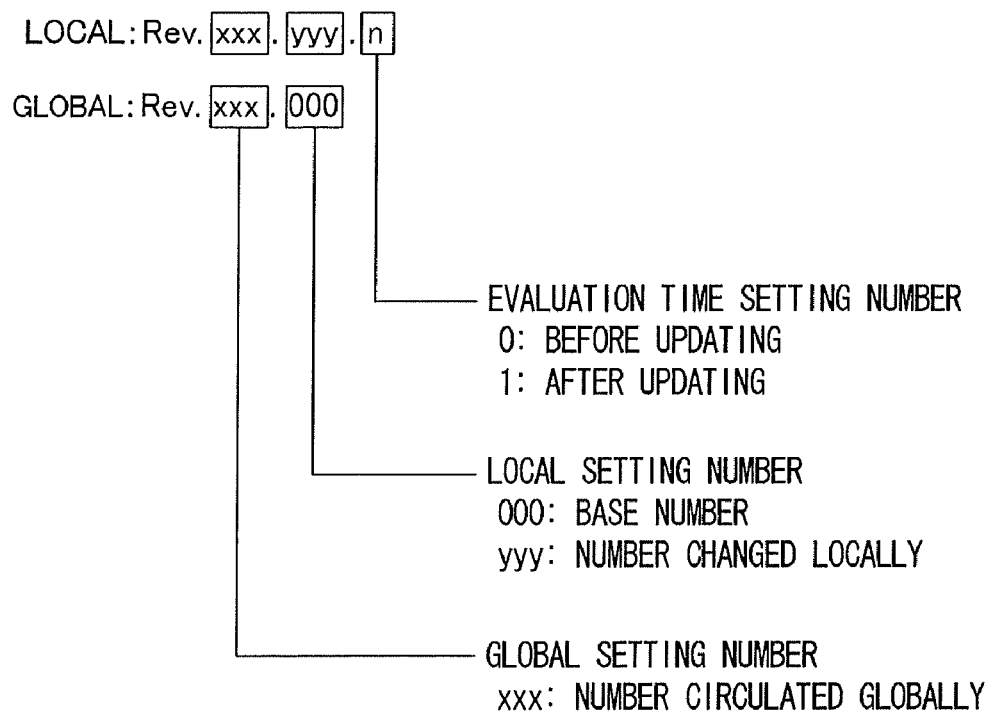
FIG. 3 is a diagram showing the definitions of revision numbers in the first embodiment of the present invention.

FIG. 3 is a diagram showing the definitions of the revision numbers in the first embodiment of the present invention.

As shown in FIG. 3, there are two categories of the revision numbers. More specifically, there are global revision numbers and local revision numbers. The global revision number is used by the supplier of the component library. In other words, the global revision numbers are used by the party which supplies the component library. The local revision numbers are used by the recipient of the component library. In other words, the local revision numbers are used by the party which is supplied with the component library.

The local revision numbers have a global setting number and a local setting number. Furthermore, the local revision numbers have an evaluation time setting number when the in-equipment component library 30 holds the in-equipment component specific data 32 before updating and the in-equipment component specific data 32 after updating. On the other hand, the global revision numbers include a global setting number and a local setting number.

Here, the global setting number and the local setting number both have three digits and the evaluation time setting number has one digit, but the numbers of digits of the respective numbers are not limited to these.

The global setting number is distributed globally, and is assigned by the supplier of the component library. This global setting number cannot be incremented by the recipient of the component library. Furthermore, the global setting number normally starts from "001", but may of course start from a number other than "001".

Normally, "000" is assigned as the local setting number by the supplier of the component library. This local setting number can be changed, and more specifically, incremented, by the recipient of the component library. Furthermore, the local setting number normally starts from "000", but may of course start from a number other than "000".

The evaluation time setting number is assigned by the recipient of the component library. This evaluation time setting number is used for distinguishing between the in-equipment component specific data 32 before and after updating. More specifically, the in-equipment component specific data 32 is updated, and when the in-equipment component specific data 32 before and after updating are held in the in-equipment component library 30, then the evaluation time setting number is assigned. In the description given here, "0" is assigned as the evaluation time setting number to the in-equipment component specific data 32 before updating, and "1" is assigned as the evaluation time setting number to the in-equipment component specific data 32 after updating, but other numbers may of course be used.

Furthermore, the global setting number and the local setting number of the in-equipment component specific data 32 before updating may be used for the global setting number and the local setting number of the updated in-equipment component specific data 32. Consequently, the in-equipment component specific data 32 before and after updating are distinguished by means of the evaluation time setting number only.

After evaluating the in-equipment component specific data 32 before and after updating, if the in-equipment component specific data 32 after updating is selected, then the local setting number of the in-equipment component specific data 32 after updating is incremented.

The in-equipment component library 30 described above is stored in the component library storage unit 29 shown in FIG. 1. More specifically, the shape data is stored in a shape data storage unit 39, the recognition parameters are stored in a recognition parameter storage unit 40, the template is stored in a template storage unit 41, the template use frequency is stored in a template use frequency storage unit 42, the match rate is stored in a match rate storage unit 43, the match reference value is stored in a match reference value storage unit 44, and the judgment threshold value data 33 is stored in a judgment threshold value data storage unit 45.

By processing the input image using the shape data, recognition parameters, template and template use frequency contained in the in-equipment component library 30, the image processing unit 27 described above carries out the inspection of the mounting state, such as the inspection of the presence or absence of a component at a prescribed position on the substrate 23, inspection to confirm whether or not an incorrect component other than a prescribed component has been mounted at a prescribed position on the substrate 23 (inspection of incorrect mounting), inspection to confirm whether or not the direction of polarity of the mounted component 24 is correct, inspection of the position of the mounted component 24, and inspection of the amount of deviation of the mounted component 24 from the ideal mounting position. The inspection of the presence or absence of a component at a prescribed position on the substrate 23 includes an inspection to confirm that no foreign material is present at a position where a component is expected to be mounted in a subsequent processing step. Since this inspection is carried out by rough recognition, then any template can be used.

More specifically, the image processing unit 27 may comprise: an edge portion extraction unit 46, a template composition/registration unit 47, a matching calculation unit 48, a component position measurement unit 49, a template selection unit 50 and a template use frequency updating/storage processing unit 51.

The edge portion extraction unit 46, the template composition/registration unit 47, the matching calculation unit 48, the component position measurement unit 49, the template selection unit 50 and the template use frequency updating/storage processing unit 51 used can be the same as those disclosed in Japanese Patent Application Publication No. 2003-110298 described above, and therefore the detailed description thereof is omitted here and only a brief explanation is given.

The edge portion extraction unit 46 extracts the edge portions of electrode portions, which are one portion of the outline of the component under inspection, from the input image. The shape data and recognition parameters are used for the extraction of the edge portions. More specifically, when extracting the edge portions, a region for determining the edge portions is set in the input image. The shape data and recognition parameters are used to set this region.

The template composition/registration unit 47 composes a template on the basis of the extracted edge portions, and registers the template thus composed in the component library storage unit 29. The shape data is used for the composition of the template.

The matching calculation unit 48 carries out the inspection of the mounting state described above by carrying out a matching process using the registered template. The position of the mounted component 24 and the amount of positional deviation of the component 24 are determined in pixel units. The recognition parameters are used for this matching process. More specifically, the recognition parameters are used in order to enlarge or reduce the template in accordance with the variation tolerance of the component 24 under inspection, or in order to alter the shape of the template to some extent.

The component position calculation unit 49 converts the position of the mounted component 24 and the amount of positional deviation of the mounted component 24, which have been determined in pixel units, into dimensions in meter units. Moreover, the component position measurement unit 49 uses the recognition parameters to create a value by adding the variation tolerance of the component 24 under inspection to the converted value.

The template selection unit 50 switches the template used for the matching process. The template use frequency updating/storage processing unit 51 updates the frequency of use of the template, and stores the frequency of use after updating in the component library storage unit 29.

This mounted component inspection apparatus includes a component library control unit 52. Information for updating the in-equipment component specific data 32 is input to this component library control unit 52. This information is generated, for example, by a user operating an input unit (not illustrated). It is possible to use a keyboard, for example, as the input unit.

When information for updating the in-equipment component specific data 32 is input, the component library control unit 52 creates updated in-equipment component specific data 32 on the basis of this information, and stores the updated in-equipment component specific data 32 thus created in the component library storage unit 29.

Furthermore, when the updated in-equipment component specific data 32 is stored in the component library storage unit 29, the component library control unit 52 assigns "0" as an evaluation time setting number to the in-equipment component specific data 32 before updating, and assigns "1" as an evaluation time setting number to the updated in-equipment component specific data 32.

Moreover, this mounted component inspection apparatus includes a result judgment unit 53. The result judgment unit 53 judges whether or not the result of the inspection by the image processing unit 27 is satisfactory. The result judgment unit 53 creates OK information if the inspection result is satisfactory and conversely, creates NG information if the inspection result is unsatisfactory. The judgment threshold value data 33 is used to judge whether or not the result is satisfactory. The judgment threshold value data 33 includes, for example, a judgment threshold value for the amount of deviation of the mounted component 24 from the ideal mounting position, and the like.

Furthermore, the result judgment unit 53 includes a match rate calculation unit 54, which is one example of a match rate acquisition unit. The match rate calculation unit 54 acquires the match rate of the in-equipment component specific data 32 used for the inspection by the image processing unit 27, on the basis of the inspection result by the image processing unit 27 and information identifying the in-equipment component specific data 32 used for the inspection. The result judgment unit 53 stores the match rate thus acquired in the component library storage unit 29.

Furthermore, when the image processing unit 27 has carried out the inspection using the in-equipment component specific data 32 before and after updating, the result judgment unit 53 evaluates the in-equipment component specific data 32, respectively. The match rates of the in-equipment component specific data 32 before and after updating are used in this evaluation. More specifically, the result judgment unit 53 selects the in-equipment component specific data 32 having a higher match rate, of the in-equipment component specific data 32 before and after updating.

In this way, the match rate is used to evaluate the in-equipment component specific data 32 before updating and the in-equipment component specific data 32 after updating, in other words, to judge which of the in-equipment component specific data 32 is suitable for the inspection by the image processing unit 27.

Furthermore, the result judgment unit 53 discards the in-equipment component specific data 32 having a lower match rate. Moreover, the result judgment unit 53 also has a function as an incrementing unit. More specifically, when the in-equipment component specific data 32 after updating is selected, then the result judgment unit 53 increments the local setting number of the in-equipment component specific data 32 after updating. Furthermore, the result judgment unit 53 discards the evaluation time setting number assigned to the in-equipment component specific data 32 left after the selection.

When the selection has been made by the result judgment unit 53, the image processing unit 27 carries out the inspection using the in-equipment component specific data 32 selected by the result judgment unit 53, after the selection step.

Furthermore, this mounted component inspection apparatus includes an evaluation period measurement unit 55 for measuring a period for which the in-equipment component specific data 32 before and after updating are evaluated. In the description given here, the evaluation period measurement unit 55 counts the number of inspections, which is the number of times that the inspection has been carried out, but the evaluation period measurement unit 55 may also count the number of times the inspection is carried out using the updated in-equipment component specific data 32. This counting process can be achieved by means of a counter, for example.

The mounted component inspection apparatus composed as described above carries out the inspection of the corresponding mounted component for the prescribed period (evaluation period), using the in-equipment component specific data 32 before updating and the in-equipment component specific data 32 after updating, and acquires their match rates. The mounted component inspection apparatus evaluates the in-equipment component specific data 32 before updating and the in-equipment component specific data 32 after updating, on the basis of the match rates thus acquired, and selects the more suitable in-equipment component specific data 32, of the in-equipment component specific data 32 before and after updating, to inspect the corresponding mounted component. After making this selection, the mounted component inspection apparatus carries out the inspection of the mounted component by using the selected in-equipment component specific data 32.

Moreover, this mounted component inspection apparatus includes a display control unit 56. The display control unit 56 issues a notification of unsatisfactory locations on the substrate 23 which are judged to be unsatisfactory (NG) by the result judgment unit 53. Furthermore, as described below, the display control unit 56 issues a notification of points of difference between the in-equipment component specific data 32 before and after updating, notification of the match rate, and notification of a match rate equal to or lower than a match reference value which is a prescribed reference value. These notifications can be made by displaying on a display monitor or on paper. The display control unit 56 thus serves as a point-of-difference notification unit and a match rate notification unit.

Moreover, this mounted component inspection apparatus includes a warning processing unit 57. This warning processing unit 57 issues a warning when the match rate is lower than the match reference value. The warning method used involves, for example, halting the related equipment, issuing an alarm, and notifying a person capable of carrying out the maintenance of the equipment by using a communications circuit such as a LAN. The timing of the warning may be a warning issued at the instant that the match rate falls below the match reference value, a warning issued when a prescribed time has elapsed after the match rate has fallen below the match reference value, or a warning issued in accordance with the frequency of the match rate falling below the match reference value.

The image processing unit 27, the component library control unit 52, the result judgment unit 53, the evaluation period measurement unit 55, the display control unit 56 and the warning processing unit 57 of this mounted component inspection apparatus may be programmed so as to be realizable in a device which executes programs, such as a personal computer.

Figure 4:
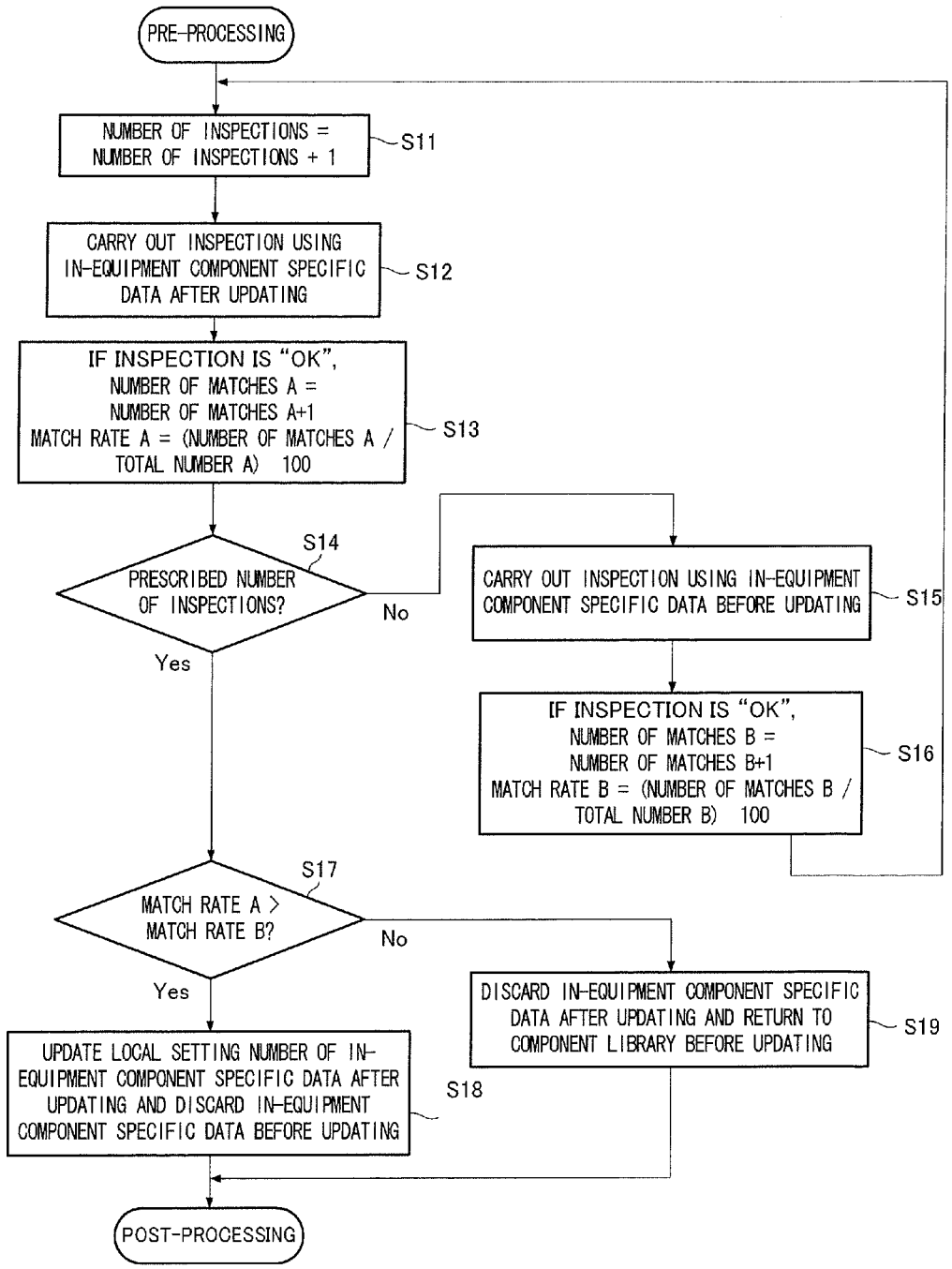
FIG. 4 is the flowchart of a mounted component inspection method in the first embodiment of the present invention.

Next, the operation of the mounted component inspection apparatus having the composition described above will be explained. Here, the operation in the event of a normal inspection is similar to the operation disclosed in Japanese Patent Application Publication No. 2003-110298 described above, and therefore, a further description thereof is omitted here and below, the operation of the mounted component inspection apparatus in evaluating the in-equipment component specific data 32 before and after updating and selecting one of these in-equipment component specific data 32 will be described with reference to FIG. 4. FIG. 4 is the flowchart of the mounted component inspection method in the first embodiment according to the present invention.

Firstly, at step S11, the number of inspections is counted by the evaluation period measurement unit 55. Thereupon, at step S12, when the image processing unit 27 has carried out an inspection using the in-equipment component specific data after updating, if the result of the inspection thus carried out is satisfactory (OK) at step S13, the match rate calculation unit 54 increments the number of matches A of the in-equipment component specific data after updating, and this number of matches A is divided by the total number of times A that the updated in-equipment component specific data has been used in the evaluation period, thereby calculating the match rate A. The match rate A represents a count value which counts the number of OK information created by the result judgment unit 53.

Next, at step S14, the evaluation period measurement unit 55 checks whether or not the number of inspections has reached a prescribed value, and if the number of inspections has not reached the prescribed value (NO), then it is judged that the evaluation period has not elapsed, the procedure transfers to step S15, and the image processing unit 27 again carries out the inspection, using the in-equipment component specific data before updating, on the component which has been inspected at step S12.

Thereupon, at step S16, if the result of the inspection carried out at step S15 is satisfactory (OK), the match rate calculation unit 54 increments the number of matches B of the in-equipment component specific data before updating, and calculates the match rate B by dividing this number of matches B by the total number of times B that the in-equipment component specific data before updating is used during the evaluation period. The match rate B represents a count value which counts the number of OK information created by the result judgment unit 53.

When the match rate B has been calculated at step S16, the procedure transfers to step S11 and the operations in step S11 to step S16 described above are repeated until the number of inspections reaches the prescribed value, in other words, until the evaluation period has elapsed.

When the evaluation period measurement unit 55 counts the number of times that the inspection has been carried out using the in-equipment component specific data 32 after updating, the number of inspections indicated by this count value becomes equal to the total number A and the total number B.

If the number of inspections has reached a prescribed value (YES) at step S14, then the procedure transfers to step S17, at which the match rate A and the match rate B are compared by the result judgment unit 53, and if the match rate A is higher than the match rate B (YES), then at step S18, the result judgment unit 53 updates the local setting number of the in-equipment component specific data 32 after updating, and discards the in-equipment component specific data 32 before updating. On the other hand, if the match rate A is smaller than the match rate B (NO), then at step S19, the result judgment unit 53 discards the in-equipment component specific data 32 after updating and hence, the in-equipment component library 30 returns to its state before updating.

In step S13 and step S16 described above, if the result of the inspection that has been carried out is unsatisfactory (NG), then the match rate is calculated without incrementing the number of matches, and the procedure then transfers to the next process.

Next, the notification of points of difference between the in-equipment component specific data 32 before and after updating will be described with reference to an example in which the points of difference are shown on a display monitor.

Figure 5:
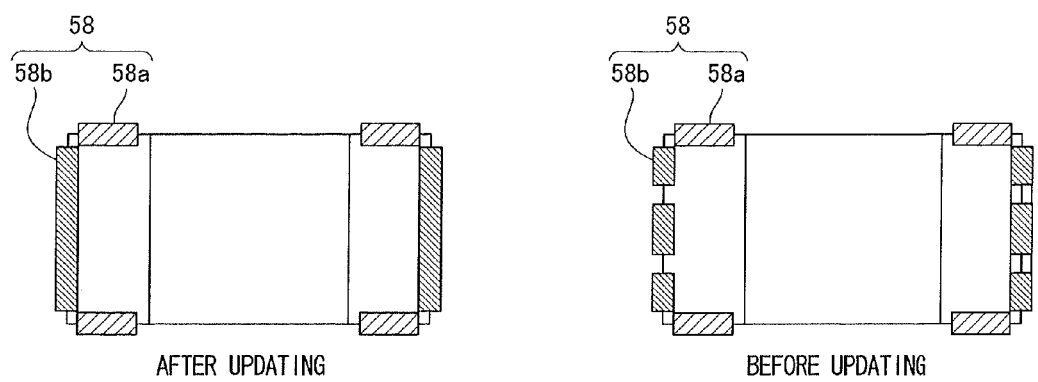
FIG. 5 is a diagram showing a display which indicates points of difference in templates before and after adjustment in the first embodiment of the present invention.

The display control unit 56 described above may show the points of difference in the shape of a template 58 on a display monitor, as shown in FIG. 5, for example, in cases where the shape of the template held in the in-equipment component specific data 32 has been changed. More specifically, for example, the display control unit 56 causes the display monitor to show the templates 58 before and after updating, side by side, with points 58a showing no difference and points 58b showing differences being displayed in different colors, or the like.

Furthermore, the display control unit 56 may show the points of difference in the recognition parameters on the display monitor, as shown in FIG. 6, for example, in cases where the recognition parameters held in the in-equipment component specific data 32 have been changed. More specifically, the display control unit 56 causes the display monitor to show the recognition parameters before and after updating, side by side, by applying underlining, or the like, to the parameters which are different. FIG. 6 shows a case where there have been changes to: size variation search values Xmin and Xmax which indicate the respective maximum variation values in the positive X direction and the negative X direction of the template, and a size variation search value Xstep which indicates the variation step width in the X direction of the template.

FIG. 6 shows one example of the recognition parameters which include, apart from the size variation search values Xmin, Xmax and Xstep described above, size variation search values Ymin and Ymax indicating the respective maximum variation values in the positive Y direction and the negative Y direction of the template, a size variation search value Ystep indicating the variation step width in the Y direction of the template, and a rough recognition limit evaluation value and a precise recognition limit evaluation value which indicate reference values for the evaluation values of the matching process, such as the degree of coincidence between the mounted component and the template. The rough recognition limit evaluation value is a reference value when the mounted component is recognized roughly in the matching process and the precise recognition limit evaluation value is a reference value when the mounted component is recognized precisely in the matching process.

Next, the notification of the match rate and the notification of a match rate equal to or lower than the match reference value will be described with reference to an example where the notifications are shown on a display monitor.

Figure 7:
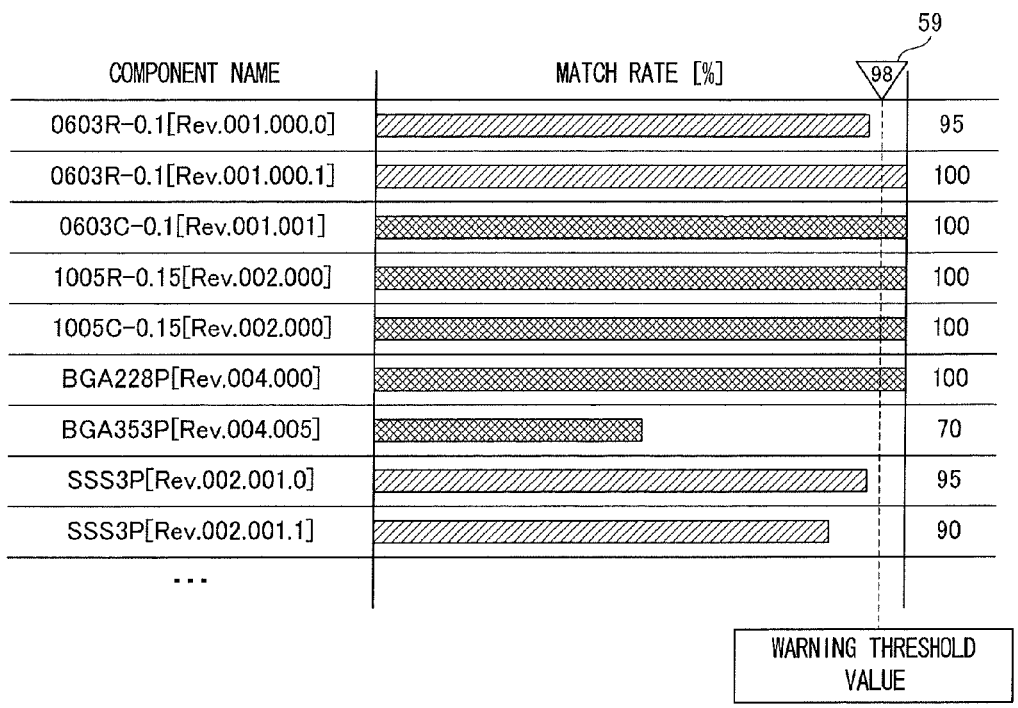
FIG. 7 is a diagram showing a display which indicates the table of a match rate in the first embodiment of the present invention.

As shown in FIG. 7, for example, the display control unit 56 described above causes a display monitor to show the table of the match rate for each component name. More specifically, the display control unit 56, for example, causes the display monitor to show a component name, the local revision number of the in-equipment component specific data 32 of that component, and the match rate held in the in-equipment component specific data 32.

Furthermore, the display control unit 56 can also cause the monitor to display the in-equipment component library currently under evaluation. FIG. 7 shows a case where the in-equipment component library of a component 0603R-0.1 and a component SSS3P is under evaluation. More specifically, for example, the display control unit 56 uses different colors for the match rate of the in-equipment component specific data under evaluation and the match rate of the other in-equipment component specific data.

Furthermore, the display control unit 56 may also cause the monitor to display a match rate equal to or lower than the match reference value, by showing a warning threshold value 59, which is the match reference value, on the display monitor, as shown in FIG. 7, for instance.

Figure 8:
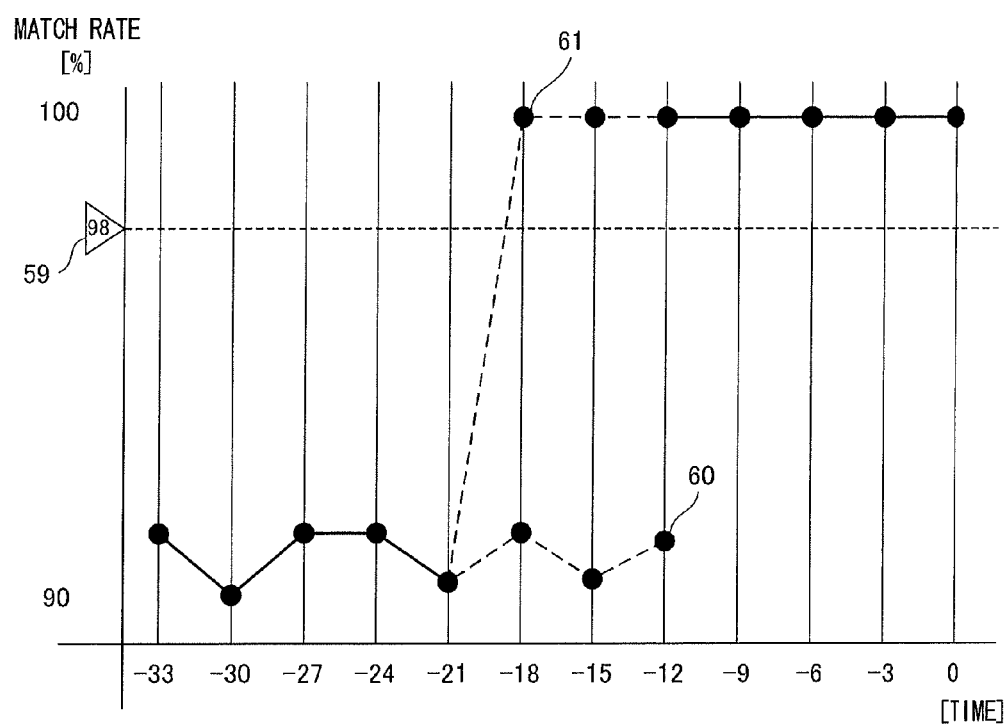
FIG. 8 is a diagram showing a display which indicates the time series graph of the match rate in the first embodiment of the present invention.

Moreover, as shown in FIG. 8, for example, the display control unit 56 may show on the display monitor the graph of the time series of the match rate. In FIG. 8, reference numeral 60 denotes the graph of the match rate of the in-equipment component specific data before updating, and reference numeral 61 denotes the graph of the match rate of the in-equipment component specific data after updating.

The display control unit 56 may also cause the display monitor to show the graph of the match rate for each prescribed unit time, if the match rates are shown as a time series. FIG. 8 shows a case where a change in the match rate every three hours is displayed.

If the in-equipment component specific data has been updated, then during the evaluation period, the graph 60 of the match rate of the in-equipment component specific data before updating and the graph 61 of the match rate of the in-equipment component specific data after updating are shown, side by side. The updating of the in-equipment component specific data is not always performed at precise time intervals. As shown in FIG. 8, for example, the graphs 60 and 61 of the match rate of the in-equipment component specific data before and after updating use a start point at −21 hours, but the actual start point does not have to be −21 hours.

In the description given here, the component library control unit 52 creates the in-equipment component specific data 32 after updating, on the basis of information input by the operator, but when the lot of components under inspection is switched, the image processing unit 27 may create a new template on the basis of the image of the component after switching, and the component library control unit 52 may use this new template to create an updated in-equipment component specific data 32. Furthermore, the component library control unit 52 may create in-equipment component specific data 32 based on a new reference component library 36 which has been delivered from the component library supplier, and may cause the in-equipment component library 30 to hold this data as updated in-equipment component specific data 32.

According to the first embodiment, in a production line in which no less than 1000 components under inspection are mounted on a single substrate, and a recognition rate of a level, at which only several false recognitions are found in a million component inspections, is required, it is possible to carry out a suitable adjustment of the in-equipment component library in accordance with the actual state of the inspection capability, in order to achieve high-level inspections.

(Second Embodiment)

Next, a second embodiment of the present invention is described in detail with reference to the drawings. Here, elements which are the same as those described in the first embodiment above are not explained, and only the points of difference from the first embodiment are described.

Figure 9:
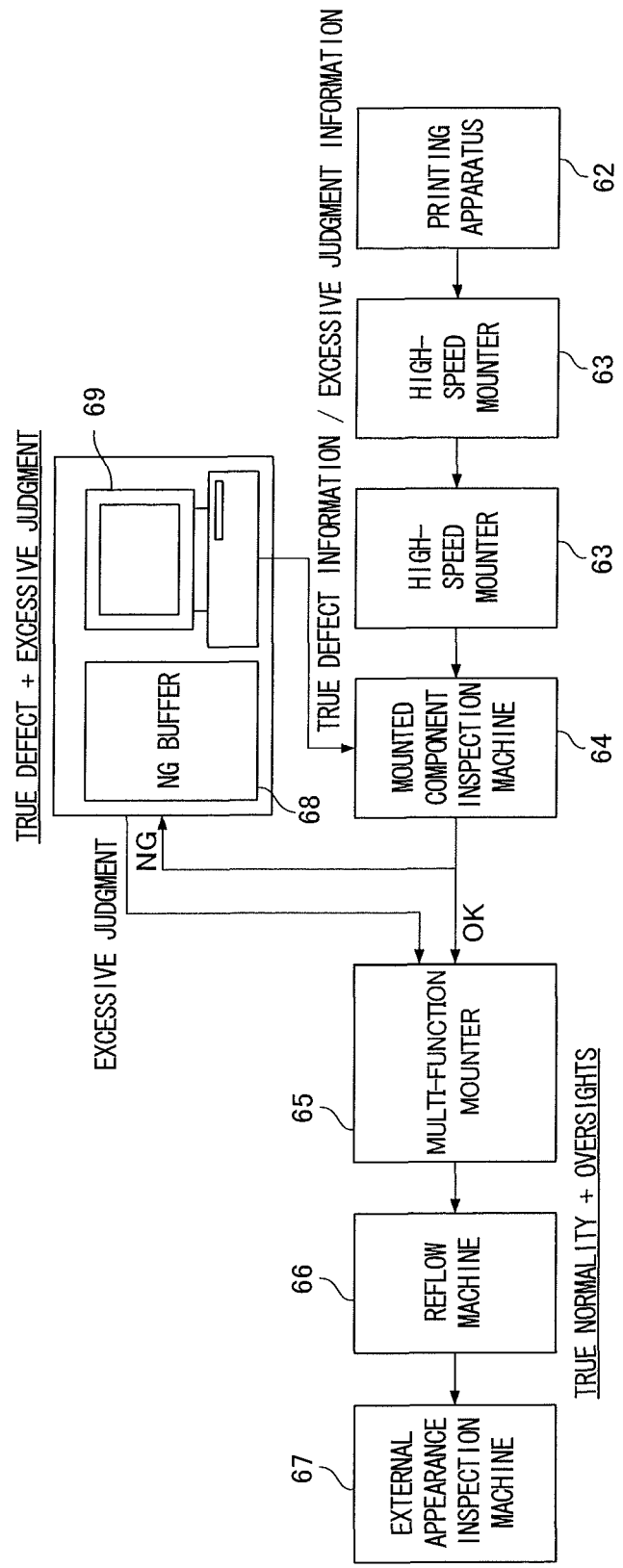
FIG. 9 is a diagram showing the overview of the composition of a mass production line for mounting components on a substrate according to a second embodiment of the present invention.

FIG. 9 is a diagram showing the overview of the composition of a mass production line for mounting components on a substrate according to the second embodiment of the present invention.

In FIG. 9, a printing machine 62 prints cream solder onto a substrate (not illustrated) which passes along the mass-production line. A high-speed mounter 63 mounts small chip components, mainly, on the substrate onto which the cream solder has been printed. A mounted component inspection machine 64 is one example of a mounted component inspection apparatus, and similarly to the first embodiment described above, the mounted component inspection machine 64 carries out the inspection of the state of mounting on the substrate on which the components have been mounted by the high-speed mounter 63, by means of image processing using the in-equipment component library 30. If the result of this inspection is satisfactory, in other words, OK, then the substrate which has been judged to be OK is conveyed to a multi-function mounter 65 in the next processing step. On the other hand, if the result of the inspection by the mounted component inspection machine 64 is unsatisfactory, in other words, NG, then the substrate which has produced the NG result is separated off to an NG buffer 68.

The multi-function mounter 65 mounts large package products on the substrate. Examples of the large package products include: QFP (Quad Flat Package), BGA (Ball Grid Array), connectors, shield cases, and the like. A reflow machine 66 solders together the substrate and the components mounted on the substrate. An external appearance inspection device 67 inspects the external appearance of the substrate to which the components have been soldered.

Unsatisfactory (NG) substrates are separated off to the NG buffer 68, as described above. A special buffer apparatus may be provided as the NG buffer 68, and the substrate may be halted on a conveyance rail between the mounted component inspection machine 64 and the multi-function mounter 65.

An NG display unit 69 clearly indicates to the operator an unsatisfactory (NG) point on an unsatisfactory (NG) substrate. FIG. 9 shows a case where the NG display unit 69 is a display monitor, but the NG display unit 69 may also be a printing apparatus, for instance. The display of the unsatisfactory (NG) point is controlled by the display control unit 56 described in the first embodiment.

The operator, for example, visually observes the substrates which have been separated off to the NG buffer 68 by reference to the unsatisfactory (NG) point indicated by the NG display unit 69, and confirms whether the point judged to be unsatisfactory (NG) by the mounted component inspection machine 64 is a true defect, or whether the judgment is excessive. The confirmed information is input to the mounted component inspection machine 64, for example, by the user operating an input unit (not illustrated). It is possible to use a keyboard, for example, as the input unit. The substrate, the judgment of which is determined to be excessive, is conveyed from the NG buffer 68 to the multi-function mounter 65.

FIG. 10 shows the table of results of the inspection by the mounted component inspection machine 64 according to the second embodiment of the present invention. As shown in FIG. 10, the results of the inspection by the inspection machine 64 may be OK or NG, and the OK result includes cases which are truly normal, and oversight cases, in other words, cases which are not actually normal but are judged to be normal by the inspection machine 64. On the other hand, the NG result includes cases which are truly unsatisfactory, and cases which are excessive judgments, in other words, cases which are not actually unsatisfactory but are judged to be unsatisfactory by the inspection machine 64. However, normally, oversights cannot be permitted and, the template and the like are composed so as to increase the number of excessive judgments and reduce the number of oversights to zero.

In the first embodiment, only the number of times that the mounted component inspection apparatus has made an OK judgment is counted, and the number of times that the mounted component inspection apparatus has made an NG judgment correctly, in other words, the number of true defects is not counted. Therefore, even in a case where in-equipment component specific data suited to the inspection is used, the match rate becomes worse if the number of true defects is large, and therefore unnecessary adjustment of the in-equipment component specific data is carried out.

Therefore, in this second embodiment, then operator checks, by visual observation or the like, the unsatisfactory (NG) substrates conveyed to the NG buffer 68, inputs to the mounted component inspection machine 64 information indicating whether there is a true defect or whether the judgment is excessive, and, if information indicating a true defect is input, increments the number of matches used to calculate the match rate.

Figure 11:
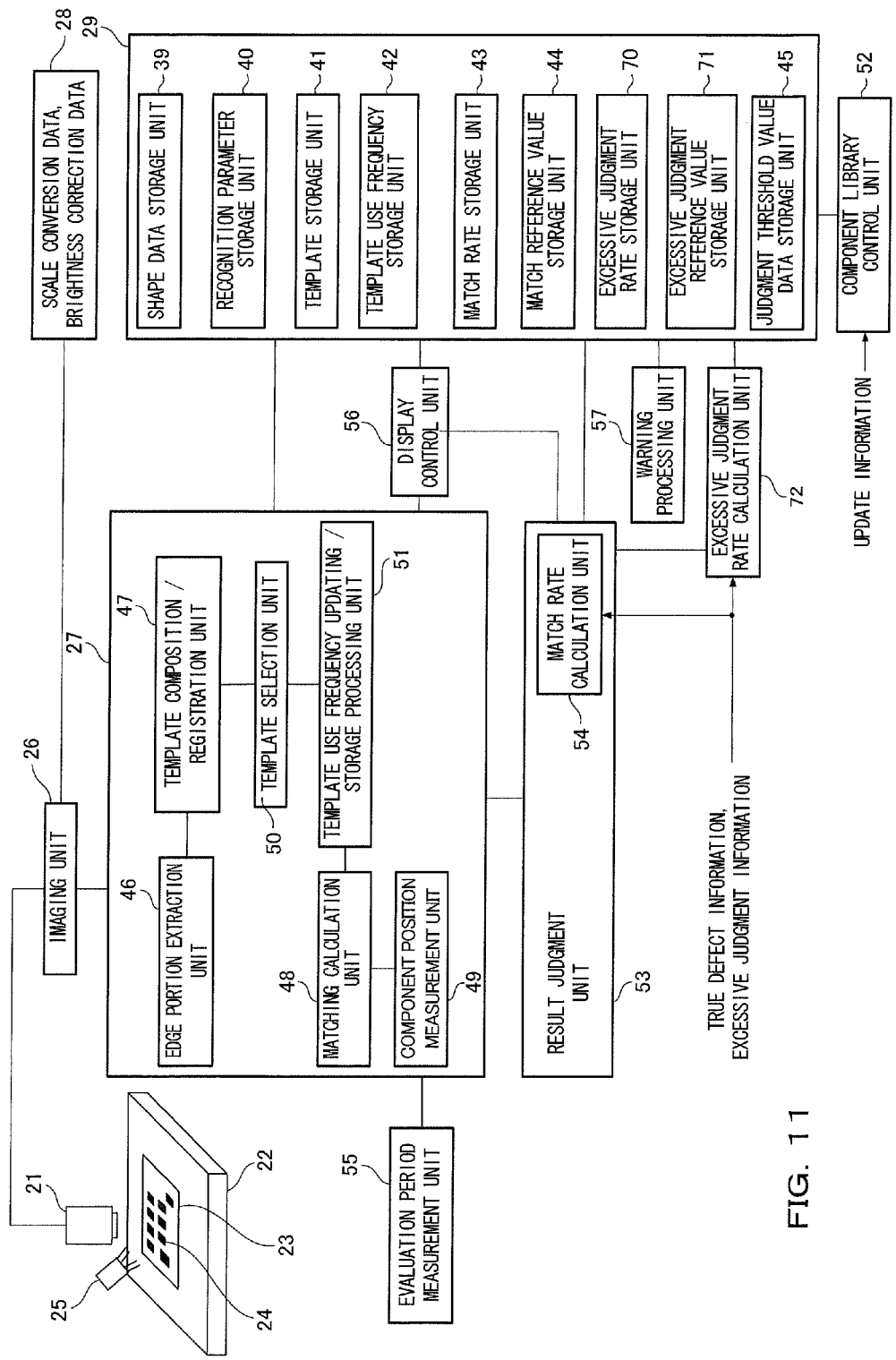
FIG. 11 is a diagram showing the overview of the composition of the mounted component inspection machine according to the second embodiment of the present invention.
Figure 12:
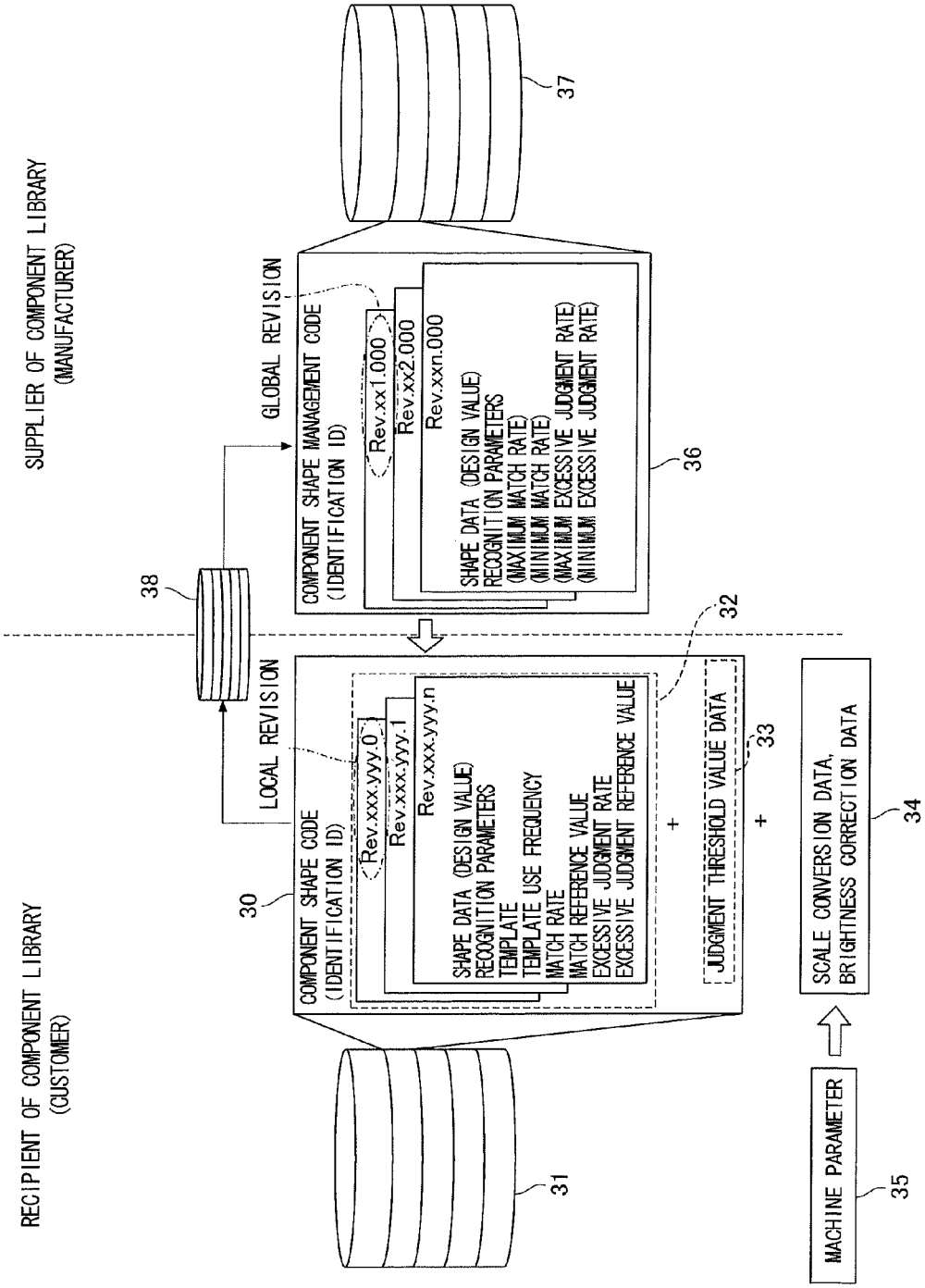
FIG. 12 is a diagram showing the overview of the composition of a component library according to the second embodiment of the present invention.

FIG. 11 is a diagram showing the overview of the composition of the mounted component inspection machine 64 according to the second embodiment of the present invention, and FIG. 12 is a diagram showing the overview of the composition of the component library according to the second embodiment of the present invention. Elements which are the same as those of the first embodiment are not described here, and only different elements will be described.

As shown in FIG. 11, the point of difference from the first embodiment is that, if the result of the inspection by an image processing unit 27 is unsatisfactory (NG), then the mounted component inspection device 64 inputs information indicating whether this unsatisfactory result is a true defect or an excessive judgment (true defect information or excessive judgment information) to a match rate calculation unit 54, and if the defect is a true defect, then the number of matches used to calculate the match rate is incremented. By this means, even if the number of true defects is large, there is no deterioration in the match rate.

Furthermore, excessive judgments are required to be reduced to a minimum. Therefore, in this second embodiment, in a similar fashion to the match rate, it is also possible to inform the operator of an excessive judgment rate indicating the rate of excessive judgments with respect to the number of times that the result of the inspection produced by the image processing unit 27 is unsatisfactory (NG). Moreover, similarly to the match rate, it is also possible to notify the operator of an excessive judgment reference value, as a warning threshold value, for judging whether or not the excessive judgment rate is satisfactory.

More specifically, as shown in FIG. 12, in-equipment component library 30 is made to retain the excessive judgment rate and the excessive judgment reference value, separately from the match rate and the match reference value. Furthermore, as shown in FIG. 12, while the in-equipment component library 30 includes real-time information of the excessive judgment rate, a reference component library 36 includes parameters of the maximum and minimum values obtained previously for the excessive judgment rate held by the in-equipment component library 30 corresponding to the reference component library 36. These parameters are updated whenever a notification is received from a recipient, if the excessive judgment rate retained by the in-equipment component library 30 of the recipient, which changes in real time, has exceeded the maximum value obtained previously, or has fallen below the minimum value obtained previously.

As shown in FIG. 11, the excessive judgment rate and the excessive judgment reference value are respectively stored in an excessive judgment rate storage unit 70 and an excessive judgment reference value storage unit 71. Furthermore, as shown in FIG. 11, the mounted component inspection machine 64 includes an excessive judgment rate calculation unit 72, which is one example of an excessive judgment rate acquisition unit. The excessive judgment rate calculation unit 72 acquires the excessive judgment rate of in-equipment component specific data 32 used for an inspection, on the basis of information indicating that the judgment of the inspection by a result judgment unit 53 is unsatisfactory (OK information/NG information), information indicating whether the unsatisfactory result is a true defect or an excessive judgment (true defect information/excessive judgment information), and information identifying the in-equipment component specific data 32 used for the inspection. The excessive judgment rate calculation unit 72 stores the excessive judgment rate thus acquired in a component library storage unit 29.

The excessive judgment rate can be calculated by a calculation method similar to that used for the match rate as described above. More specifically, when the inspection using the in-equipment component specific data has been carried out, if the result of the inspection carried out is unsatisfactory (NG), and if the result is not a true defect but an excessive judgment; then the excessive judgment rate calculation unit 72 increments the excessive judgment number in the in-equipment component specific data, and calculates the excessive judgment rate by dividing this excessive judgment number by the number of times that the result judgment unit 53 has judged the result of the inspection carried out using the in-equipment component specific data to be unsatisfactory. The excessive judgment number represents the count value obtained by counting information indicating that the unsatisfactory result is not a true defect but an excessive judgment, and the excessive judgment rate indicates the ratio in which excessive judgments are made.

Furthermore, a display control unit 56 also issues the notification of the excessive judgment rate and the notification of an excessive judgment rate equal to or higher than an excessive judgment reference value, which is a prescribed reference value, similarly to the notification of the match rate and the notification of a match rate equal to or lower than a match reference value, which is a prescribed reference value. The display control unit 56 thus serves as an excessive judgment rate notification unit.

Similarly to the notification of the match rate, the notification of the excessive judgment rate may be issued by displaying the table of the excessive judgment rate for each component name on a display monitor or the like, or by displaying the graph of the time series of the excessive judgment rates on a display monitor or the like.

Furthermore, similarly to the notification of the match rate, when the table of the excessive judgment rate for each component name is shown on a display monitor or the like, then the in-equipment component library currently under evaluation may be indicated by, for example, using different colors to show the excessive judgment rate of the in-equipment component specific data under evaluation and the excessive judgment rate of the other in-equipment component specific data. Moreover, by showing a warning threshold value, which is an excessive judgment reference value, an excessive judgment rate equal to or higher than the excessive judgment reference value may be indicated.

Furthermore, similarly to the notification of the match rate, when the excessive judgment rate is displayed as a time series, then the excessive judgment rate for each prescribed unit time may be displayed as a graph.

In this way, by notifying the operator of the excessive judgment rate and the excessive judgment reference value used to judge whether or not the excessive judgment rate is satisfactory, then the operator's attention is drawn more readily to excessive judgments.

The excessive judgment rate calculation unit 72 may be programmed so as to be realizable in a device for executing programs, such as a personal computer.

As described above, according to the second embodiment, rather than calculating the match rate of the in-equipment component specific data only by judging the inspection result from the mounted component inspection machine 64, the match rate is calculated using information about true defects, and therefore it is possible to improve the accuracy of the match rate if there is a large number of true defects. Furthermore, since the excessive judgment rate is calculated using information on excessive judgments and the excessive judgment rate thus calculated is notified to the operator, then it is possible to adjust the in-equipment component library with particular attention to excessive judgments.

Figure 13:
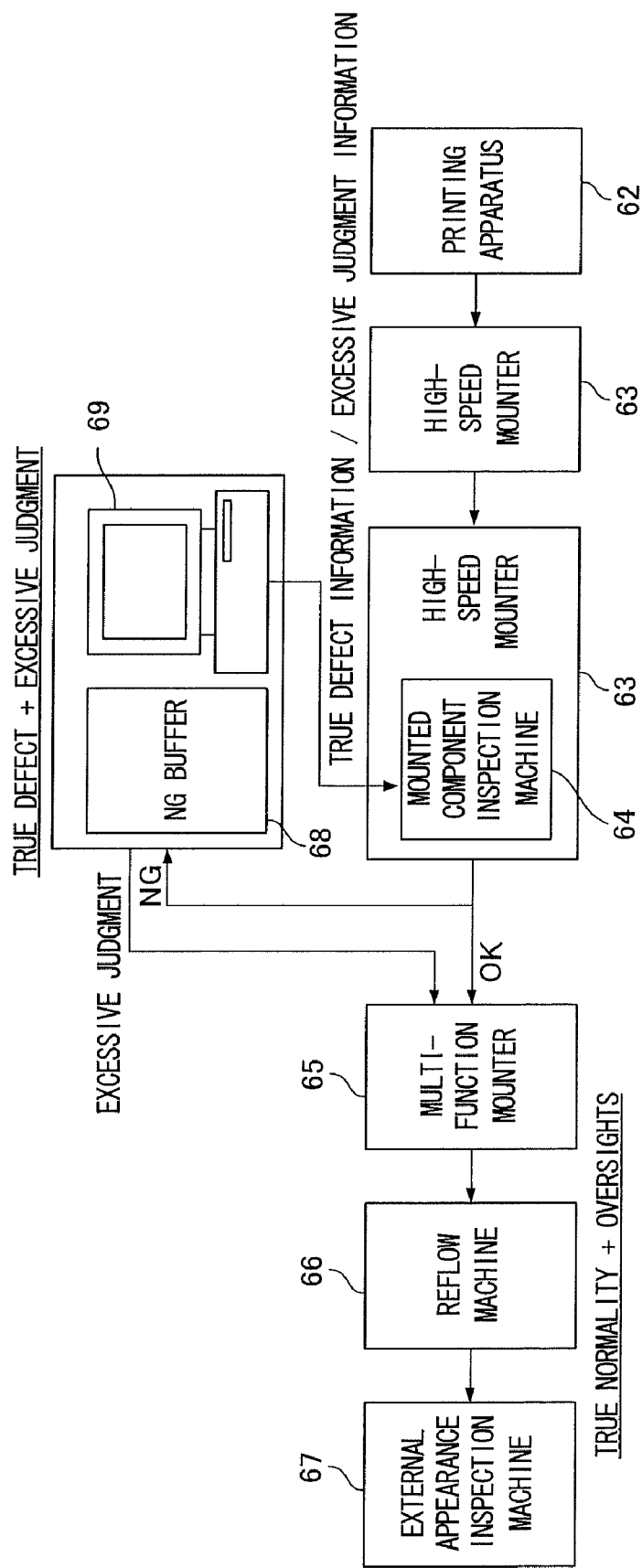
FIG. 13 is a diagram showing the overview of a further composition of the mass production line according to the second embodiment of the present invention.

In the description given above, the mounted component inspection machine 64 is disposed independently between the high-speed mounter 63 and the multi-function mounter 65, but as shown in FIG. 13, for example, the mounted component inspection machine 64 may be provided in the high-speed mounter 63. This high-speed mounter 63 is capable of carrying out the inspection of mounted components by means of the mounted component inspection machine 64.

(Third Embodiment)

Next, a third embodiment of the present invention is described in detail with reference to the drawings. Detailed descriptions of items which are the same as those described in the first and second embodiments are not given here.

Figure 14:
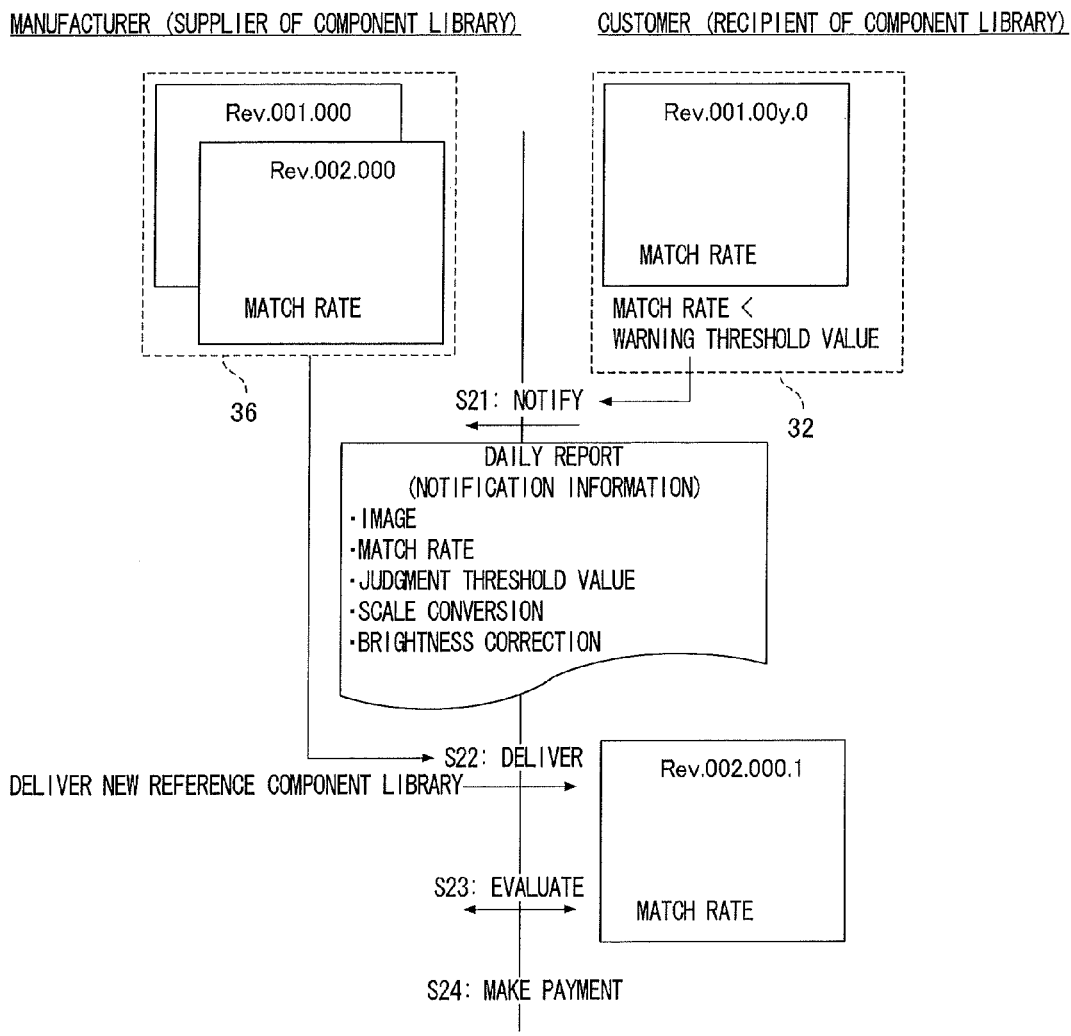
FIG. 14 is a diagram showing a method of delivering a component library according to a third embodiment of the present invention.
Figure 15:
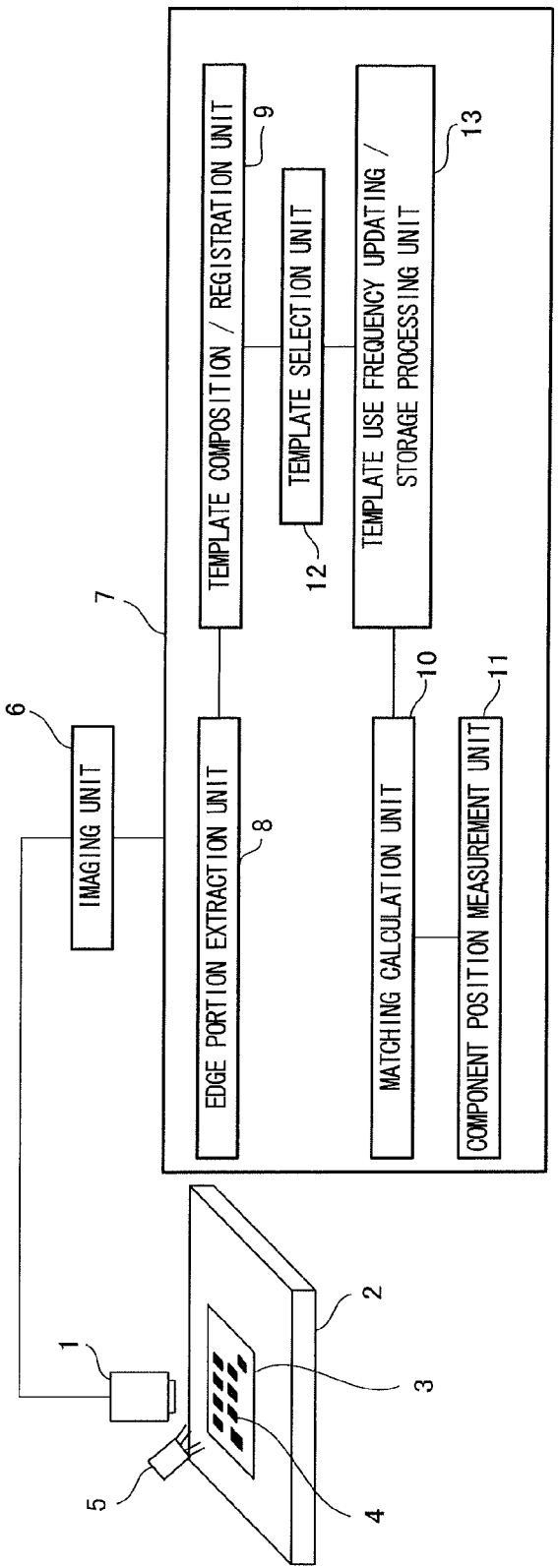
FIG. 15 is a diagram showing the composition of a conventional mounted component inspection apparatus.

FIG. 14 is a diagram showing a method of delivering a component library according to the third embodiment of the present invention.

In FIG. 14, a customer (recipient of a component library) signs a component library support contract with a manufacturer (supplier of the component library).

If the match rate of the component library used by the customer is lower than a warning threshold value, then the customer issues a notification to the manufacturer (step S21). More specifically, the customer gathers on a daily basis, in the form of daily reports, false recognition images where recognition has not been made accurately, of the images of components presenting a problem, and the customer reports these false recognition images to the manufacturer, together with the match rate at the time when the images were captured, judgment threshold value data 33, and equipment specific data 34 comprising scale conversion data and brightness correction data.

The customer uses the gathered false recognition images as daily reports for informing about the daily inspection status. On the other hand, as described above, the manufacturer receives the notification of the false recognition images, together with the match rate, the judgment threshold value data 33, the scale conversion data and the brightness correction data, and the manufacturer can replicate the inspection status of the customer.

Upon receiving this notification, the manufacturer checks whether or not an updated reference component library is present in a reference component library 36 for the component in question, and if an updated reference component library is present, then a mounted component inspection is carried out using this library. If, as a result of this inspection, the false recognition of the customer is eliminated, the updated reference component library is delivered (step S22).

Upon receiving this delivery, the customer employs both the in-equipment component specific data which has been used previously for a prescribed period of time, and the in-equipment component specific data based on the delivered reference component library, in combination, to evaluate the match rate of these in-equipment component specific data (step S23). The excessive judgment rate may also be used for the evaluation. The result of this evaluation is delivered to the manufacturer.

If the match rate of the in-equipment component specific data based on the delivered reference component library is higher than the match rate of the in-equipment component specific data used previously, then the manufacturer issues a payment request to the customer, for example (step S24).

After the customer receiving the payment request has made payment, the customer can officially use the in-equipment component specific data based on the updated reference component library, and substitutes this data for the in-equipment component specific data used previously. On the other hand, if payment by the customer has not been confirmed within a prescribed period, the use of the delivered reference component library is not permitted and the customer returns to the in-equipment component specific data that has been used previously.

At step S22, if there is no updated reference component library, then the manufacturer may newly update the component library and deliver the same in accordance with the terms of the contract between the manufacturer and the customer. Similarly, at step S23, even if the match rate of the in-equipment component specific data based on the delivered reference component library is lower than the match rate of the in-equipment component specific data used previously, then the manufacturer can newly update the component library and deliver the same in accordance with the terms of the contract between the manufacturer and the customer.

Furthermore, since the manufacturer supports only in-equipment component specific data 32 separated from equipment specific data 34, then it the manufacture does not have to create data which is adjusted for each piece of equipment.

As described above, according to this third embodiment, even if there is no specialist operator having sufficient expertise, the manufacturer can assess the condition of the customer's inspection machine for each component shape in a numerical value indicating the match rate, and can provide the most recent reference component library in the manufacturer's possession, successively, and therefore the inspection machine can be operated at a high level.

Several exemplary embodiments according to the present invention are described above in detail, but it is easily recognized that a person skilled in the art could make various modifications to the exemplary embodiments, without substantially departing from the novel teachings of the present invention or the beneficial effects of the present invention. Consequently, it is intended that various modifications of this kind are also included in the scope of the present invention.

What is claimed is:

1. A mounted component inspection apparatus comprising:
an inspection processing unit for carrying out an inspection of a component by using a component library holding updatable inspection information;
a match rate acquisition unit for acquiring, respectively for inspection information before and after updating held by the component library, a match rate that indicates a degree to which inspection information is suitable for an inspection by the inspection processing unit, on a basis of results of inspections by the inspection processing unit; and
a judgment unit for selecting the inspection information having a higher match rate, of the inspection information before updating and the inspection information after updating, wherein the component library can hold the inspection information before and after updating, after carrying out inspections of components using the inspection information before and after updating held in the component library, the inspection processing unit carries out an inspection of a component using inspection information selected by the judgment unit, and each match rate of the inspection information before and after updating is a value obtained by dividing a count value obtained by counting the number of times that acceptable information is generated, the acceptable information indicating that a result of an inspection by the inspection processing unit using the inspection information is satisfactory, by a total number of times that the inspection information has been used.

2. The mounted component inspection apparatus according to claim 1, further comprising a component library control unit for, when information for updating the inspection information is input, causing the component library to hold the inspection information updated on a basis of the input information.

3. The mounted component inspection apparatus according to claim 1, further comprising a point of difference reporting unit for reporting points of difference in the inspection information before and after updating.

4. The mounted component inspection apparatus according to claim 1, further comprising a match rate reporting unit for reporting the respective match rates of the inspection information before and after updating acquired by the match rate acquisition unit.

5. The mounted component inspection apparatus according to claim 1, further comprising an excessive judgment rate acquisition unit for acquiring an excessive judgment rate indicating a ratio of excessive judgments that have been made, on a basis of information indicating that the judgment is excessive.

6. The mounted component inspection apparatus according to claim 5, wherein the excessive judgment rate is a value obtained by dividing a count value obtained by counting a number of times that the information indicating that the judgment is excessive is input, by a number of times that the inspection processing unit has judged results of inspections to be unsatisfactory.

7. The mounted component inspection apparatus according to claim 1, wherein a revision number is assigned to the inspection information, and the revision number has a global setting number assigned by a supplier of the component library and a local setting number which can be changed by a recipient of the component library.

8. The mounted component inspection apparatus according to claim 7, further comprising an incrementing unit for, when the inspection information after updating is selected by the judgment unit, incrementing the local setting number assigned to the inspection information after updating.

9. The mounted component inspection apparatus according to claim 1, further comprising a component library control unit for assigning, to the inspection information before and after updating, an evaluation time setting number for distinguishing between before updating and after updating.

10. A component mounting machine for mounting components on a substrate, comprising the mounted component inspection apparatus according to claim 1, wherein the components mounted on the substrate are inspected by the mounted component inspection apparatus.

11. A mounted component inspection method, comprising:
carrying out inspections of components by using inspection information before and after updating held in a component library;
acquiring, respectively for the inspection information before and after updating, a match rate indicating a degree to which the inspection information is suitable for an inspection of a component, on a basis of results of the inspections thus carried out;
selecting the inspection information having a higher match rate, on a basis of the respective match rates of the inspection information before and after updating thus acquired; and
inspecting the component using the inspection information thus selected,
wherein each match rate of the inspection information before and after updating is a value obtained by dividing a count value obtained by counting a number of times that acceptable information is generated, the acceptable information indicating a satisfactory result of an inspection using the inspection information, by a total number of times that the inspection information has been used.

12. The mounted component inspection method according to claim 11, wherein, when information for updating the inspection information is input, inspection information that is updated on a basis of the input information is held in the component library.

13. The mounted component inspection method according to claim 12, wherein the information for updating the inspection information is input when a lot of components is changed.

14. The mounted component inspection method according to claim 11, wherein inspection information having a lower match rate, of the inspection information before and after updating, is discarded from the component library.

15. The mounted component inspection method according to claim 11, wherein a revision number is assigned to the inspection information, and the revision number comprises a global setting number assigned by a supplier of the component library and a local setting number which can be changed by a recipient of the component library.

16. The mounted component inspection method according to claim 15, wherein, when the inspection information after updating is selected, the local setting number assigned to the inspection information after updating is incremented.

17. The mounted component inspection method according to claim 11, wherein, when the inspection information is updated, an evaluation time setting number for distinguishing between before updating and after updating is assigned to the inspection information before and after updating.

18. The mounted component inspection method according to claim 11, wherein the component is inspected using, together with the component library, scale conversion data and brightness correction data which are specific to equipment.

* * * * *